US00PP36179P2

(12) United States Plant Patent
Giesen

(10) Patent No.: US PP36,179 P2
(45) Date of Patent: Oct. 1, 2024

(54) ***PETUNIA* PLANT NAMED 'PEHY0083'**

(50) Latin Name: *Petunia hybrida*
Varietal Denomination: PEHY0083

(71) Applicant: SYNGENTA CROP PROTECTION AG, Basel (CH)

(72) Inventor: Eric Giesen, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 18/445,814

(22) Filed: Feb. 13, 2024

(51) Int. Cl.
*A01H 5/02* (2018.01)
*A01H 6/82* (2018.01)

(52) U.S. Cl.
USPC ..... Plt./356.22

(58) Field of Classification Search
USPC ..... Plt./263.1, 356.1, 356.13, 356.22
See application file for complete search history.

(56) References Cited

U.S. PATENT DOCUMENTS

PP30,317 P3 * 3/2019 Kleinwee ..... A01H 6/824
Plt./356.21

* cited by examiner

*Primary Examiner* — Karen M Redden
(74) *Attorney, Agent, or Firm* — Dale Skalla

(57) ABSTRACT

A new *Petunia* plant named 'PEHY0083' particularly distinguished by its very vigorous plant, medium size flowers, a pink flower color with a white centre, is rather late flowering and has a strong trailing plant habit.

1 Drawing Sheet

Latin name of the genus and species of the plant claimed: *Petunia hybrida.*

Varietal denomination: 'PEHY0083'.

BACKGROUND OF THE NEW PLANT

The present invention comprises a new *Petunia*, botanically known as *Petunia hybrida*, and hereinafter referred to by the variety name 'PEHY0083'.

'PEHY0083' is a product of a planned breeding program. The new cultivar has very vigorous plant size, medium sized flowers, a pink flower color with a white centre, is rather late flowering and has a strong trailing plant habit.

'PEHY0083' originated from a hybridization made in October 2016 in a controlled breeding environment in Enkhuizen, The Netherlands. The female parent was the proprietary selection 'N4317-1', not patented. Compared to 'PEHY0083', it has more semi trailing plant shape, salmon flower color, and larger flowers.

The male parent of 'PEHY0083' was the proprietary selection 'BB0391-21V', not patented. Compared to 'PEHY0083', it is more vigorous, later in flowering, and it has a dark rose flower color with a larger white centre.

The resulting seeds were sown in February 2017. 'PEHY0083' was selected as one flowering plant within the progeny of the stated cross in May 2017 in a controlled environment in Enkhuizen, The Netherlands.

The first act of asexual reproduction of 'PEHY0083' was accomplished when vegetative stem cuttings were propagated from the initial selection in January 2018 in a controlled environment in Enkhuizen, The Netherlands.

BRIEF SUMMARY OF INVENTION

Horticultural examination of plants grown from cuttings of the plant initiated in January 2018 and continuing thereafter, has demonstrated that the combination of characteristics as herein disclosed for 'PEHY0083' are firmly fixed and are retained through successive generations of asexual reproduction.

'PEHY0083' has not been observed under all possible environmental conditions. The phenotype may vary significantly with variations in environment such as temperature, light intensity, and day length.

A Plant Breeder's Right for this cultivar was applied for in the European Union on Dec. 19, 2023, No. 20232785. 'PEHY0083' has not been made publicly available more than one year prior to the filing of this application.

The following traits have been repeatedly observed and are determined to be basic characteristics of the new variety. The combination of these characteristics distinguishes this *Petunia* as a new and distinct variety.

BRIEF DESCRIPTION OF THE PHOTOGRAPHS

The accompanying photographic drawing shows typical flower and foliage characteristics of 'PEHY0083' with colors being as true as possible with an illustration of this type.

Figure 1:
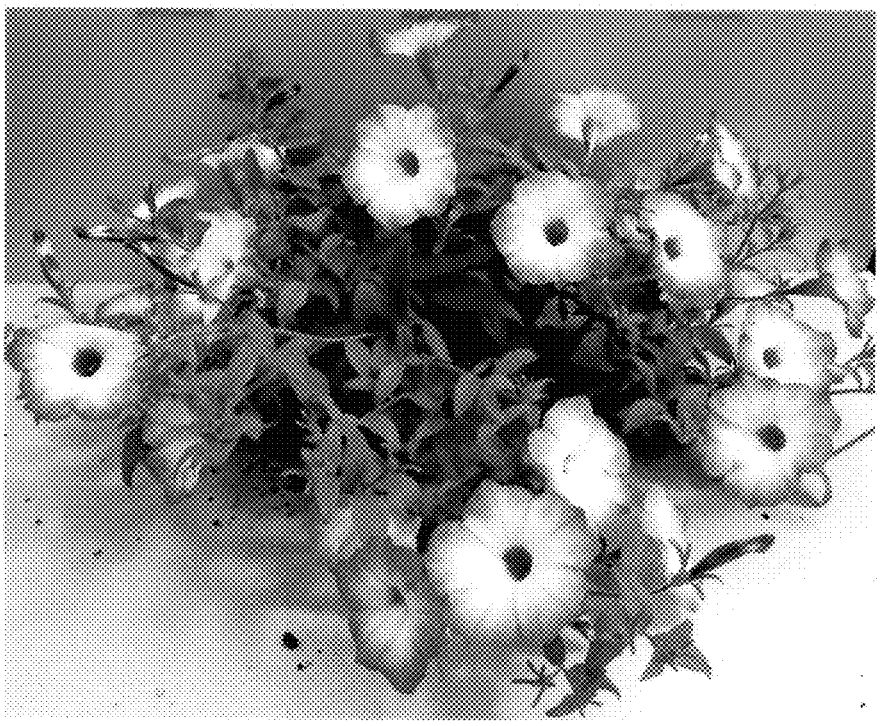
Figure 2:
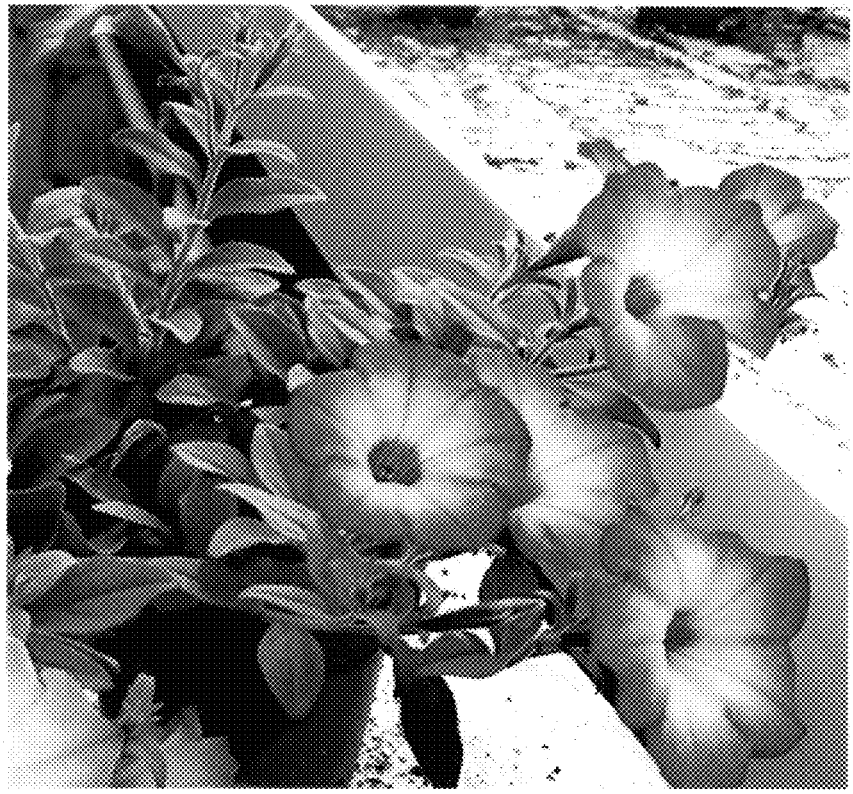

The photographic drawings show in FIG. 1 a flowering plant of the new variety and in FIG. 2 a close-up of the flowers.

DETAILED BOTANICAL DESCRIPTION

The afore mentioned photographs were taken in April 2019 from plants growing indoor in 12 cm pots in Andijk, The Netherlands. These plants were approximately 12 weeks of age.

The plant descriptions and measurements were taken in July 2023 in Enkhuizen, The Netherlands on outdoor plants grown in full soil. These plants were about 16 weeks old.

Color references are made to The Royal Horticultural Society Colour Chart (R.H.S.) 2001.

TABLE 1

DIFFERENCES BETWEEN THE NEW VARIETY 'PEHY0083' AND A SIMILAR VARIETY

| | 'PEHY0083' | 'Vista Bubblegum', U.S. Plant Pat. No. 17,730 |
|---|---|---|
| Flower color: | Pink with white centre | Pink |
| Veins in flower: | Hardly any veins | Medium veined |
| Flower size: | Medium size | Medium to small flower |

Plant:

*Form, growth, and habit*.—Strong trailing plant habit.
*Plant height*.—16 cm.
*Plant height* (*inflorescence included*).—22 cm.
*Plant diameter* (*width*).—Approximately 55 cm.

Roots:

*Number of days to initiate and produce roots*.—14 days at about 22° C.
*Type*.—Fine, fibrous, free branching.
*Color*.—RHS N158C.

Foliage:

*Arrangement*.—Alternate, simple; sometimes opposite, decussate.
*Immature leaf, color upper surface*.—RHS 137C.
*Immature leaf, color lower surface*.—RHS 137B.
*Mature leaf, color upper surface*.—RHS 137C.
*Mature leaf, color lower surface*.—RHS 137D.
*Length*.—4.2-5.2 cm.
*Width*.—1.8 cm.
*Shape*.—Ovate.
*Base shape*.—Acuminate.
*Apex shape*.—Acute.
*Margin*.—Entire.
*Texture, upper surface*.—Densely covered with short hairs.
*Lower surface*.—Densely covered with short hairs.
*Color of veins, upper surface*.—RHS 137D.
*Color of veins, lower surface*.—RHS 137D.
*Petiole color*.—RHS 137D.
*Length*.—0.3 cm.
*Diameter*.—0.3 cm.
*Petiole texture*.—Densely covered with short hairs.

Stem:

*Quantity of main branches per plant*.—4-5.
*Color of stem*.—RHS 137B, RHS 147B on old stem parts.
*Length of stem*.—26 cm.
*Diameter*.—0.3-0.4 cm.
*Length of internodes*.—1.5-2.5 cm.
*Texture*.—Dense, mostly glandular short hairs.
*Color of pedicel*.—RHS 137D.
*Length of pedicel*.—2.6 cm.
*Diameter of pedicel*.—0.2 cm.
*Texture of pedicel*.—Densely covered with short hairs.

Inflorescence:

*Type*.—Flowers solitary in upper leaf axis.
*Flower type*.—Funnel-shaped; 5 lobed petals. fused at base.
*Blooming habit*.—Rather late flowering in greenhouse, flowering throughout the summer months.
*Quantity of inflorescences per plant*.—Approximately 48.
*Lastingness of individual blooms on the plant*.—About 7 days.
*Fragrance*.—Very faint.

Bud (just when opening):

*Color*.—RHS N78A at top, RHS N78B towards base.
*Length*.—4.4 cm.
*Width*.—0.7 cm.
*Shape*.—Oblong.

Immature inflorescence:

*Flower horizontal diameter*.—5.4 cm.
*Color petals, upper surface*.—RHS 74A.
*Color petals, lower surface*.—RHS 73C.

Mature flower:

*Flower horizontal diameter*.—5.5 cm.
*Flower height* (*vertical*).—4.0 cm.
*Color upper surface*.—Primary color; RHS 78D secondary color; RHS 158A (White centre).
*Color lower surface*.—RHS 78C.
*Conspicuousness of veins*.—Very little.
*Apex shape*.—Acuminate.
*Margin*.—Entire.
*Waviness of margin*.—Medium.
*Petal lobation*.—Weak.
*Petal texture, upper surface*.—Smooth.
*Petal texture, lower surface*.—Smooth, occasionally a short hair mainly along veins.
*Corolla tube color outside*.—RHS 78A.
*Corolla tube color inside*.—RHS 78A deep in throat; RHS 78C toward petals; veins RHS 81A.
*Conspicuousness of veins in tube*.—Strong.
*Corolla tube length*.—2.9 cm.
*Corolla tube texture, outside*.—Dense and short glandular hairs.
*Corolla tube texture, inside*.—Glabrous.

Calyx:

*Color of sepal, upper surface*.—RHS 137A.
*Color of sepal, lower surface*.—RHS 137B.
*Length*.—1.2 cm.
*Width*.—0.2-0.3 cm.
*Shape*.—Ensiform.
*Apex shape*.—Acute.
*Base*.—Fused.
*Margins*.—Entire.
*Texture, upper surface*.—Covered with short glandular hairs.
*Lower surface*.—Covered with short glandular hairs.

Reproductive organs:

*Pistil*.—1.
*Length*.—2.1 cm.
*Style color*.—RHS 148B.
*Style length*.—1.9 cm.
*Stigma color*.—RHS 87A, RHS 88A in centre of stigma.
*Stamens*.—
*Quantity per flower*.—5.
*Color of filaments*.—RHS 151D, 137D towards base.
*Length filaments*.—2.0 cm.
*Anther color*.—RHS 81C.
*Anther length*.—0.2 cm.

*Anther shape*.—Elliptical.
*Color of pollen*.—RHS 82B.
*Pollen amount*.—Abundant.
*Fertility/seed set*.—Has not been observed on this hybrid.
*Disease/pest resistance*.—Has not been observed on this hybrid.

What is claimed is:

1. A new and distinct variety of *Petunia* plant named 'PEHY0083' substantially as illustrated and described herein.

* * * * *